(12) United States Patent
Weaver

(10) Patent No.: US 9,103,791 B1
(45) Date of Patent: Aug. 11, 2015

(54) THALLIUM FLUORESCENT ION INDICATOR AND ASSAY

(71) Applicant: Vanderbilt University, Nashville, TN (US)

(72) Inventor: Charles David Weaver, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 20 days.

(21) Appl. No.: 14/038,606

(22) Filed: Sep. 26, 2013

Related U.S. Application Data

(60) Provisional application No. 61/706,080, filed on Sep. 26, 2012.

(51) Int. Cl.
*C07D 311/82* (2006.01)
*G01N 21/64* (2006.01)

(52) U.S. Cl.
CPC .................................. *G01N 21/6486* (2013.01)

(58) Field of Classification Search
CPC .............................. C07D 311/82; G01N 21/64
USPC .................................................... 549/200, 223
See application file for complete search history.

(56) References Cited

U.S. PATENT DOCUMENTS

| 6,162,931 A | 12/2000 | Gee et al. |
| 2002/0168625 A1 | 11/2002 | Weaver |
| 2010/0279314 A1 | 11/2010 | Beacham et al. |

OTHER PUBLICATIONS

Sigma-Aldrich Handbook of Dyes, Stains, and Indicators (Floyd G. Green, 1990, St. Louis, Mo., USA).

Gee et al., "Measuring zinc in living cells.: A new generation of sensitive and selective fluorescent probes," Cell Calcium; 2002, 31(5): 245-251.

*Primary Examiner* — Golam M M Shameem
(74) *Attorney, Agent, or Firm* — Michael Best & Friedrich LLP

(57) ABSTRACT

Disclosed are fluorescent indicators and methods for detecting the activity of an ion channel or transporter in a cell. The indicators and methods may be used to measure influx or efflux of thallium through an ion channel or a transporter.

1 Claim, 2 Drawing Sheets

THALLIUM FLUORESCENT ION INDICATOR AND ASSAY

CROSS REFERENCE TO RELATED APPLICATION

This application claims priority to U.S. Provisional Application No. 61/706,080, filed Sep. 26, 2012, the contents of which are herein incorporated by reference.

TECHNICAL FIELD

The present disclosure relates generally to thallium indicator compounds and compositions, methods of using the compounds and compositions, and processes for preparing the compounds and compositions.

BACKGROUND

Ion channels are transmembrane proteins that mediate transport of ions across cell membranes. These channels are pervasive throughout most cell types and important for regulating cellular excitability and homeostasis. Ion channels participate in numerous cellular processes such as action potentials, synaptic transmission, hormone secretion, and muscle contraction. Many important biological processes in living cells involve the translocation of cations, such as calcium ($Ca^{2+}$), potassium ($K^+$), and sodium ($Na^+$) ions, through ion channels. Cation channels represent a large and diverse family of ion channels that are recognized as important drug targets.

Movement of physiologically relevant substrates through ion channels can be traced by a variety of physical, optical, or chemical techniques. Optical methods permit measurement of the entire course of ion flux in a single cell as well as in groups of cells. The advantages of monitoring transport by fluorescence techniques include the high level of sensitivity of these methods, temporal resolution, modest demand for biological material, lack of radioactivity, and the ability to continuously monitor ion transport to obtain kinetic information.

Thallium-sensitive, fluorescence-based assays are available for identifying modulators of ion channels, channel-linked receptors or ion transporters. For example, U.S. Patent Publication No. 20020168625, which is incorporated by reference herein, describes the use of thallium to measure ion channel activity for potassium, sodium, calcium, and other ions; and U.S. Patent Publication No. 20100279314, which is incorporated by reference herein, provides additional background on the use of thallium reagents and assays.

Despite available assays and indicators, there exists a need for improved compounds, compositions, and methods for screening agents that modulate cation channel activity. Moreover, there exists a need for improved high throughput screening methods to screen large libraries or groups of potential modulators.

SUMMARY

In one aspect, disclosed is a compound of formula (I),

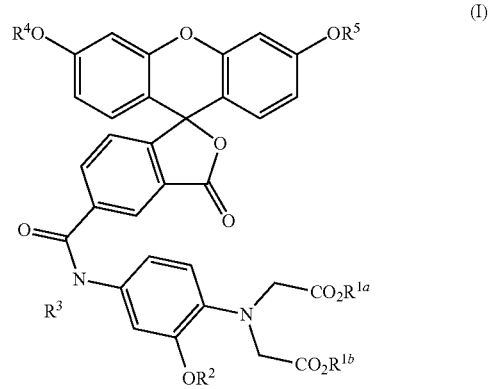

or a salt, ester, or amide thereof,
wherein $R^{1a}$ and $R^{1b}$ are each independently selected from the group consisting of H, alkyl, hydroxyalkyl, aminoalkyl, alkylaminoalkyl, di(alkyl)aminoalkyl, alkoxyalkyl, alkylcarbonyl, alkoxycarbonyl, alkylcarbonyloxyalkyl, alkenyl, alkynyl, and a counterion;

$R^2$ is selected from the group consisting of H, alkyl, alkylcarbonyl, and a counterion;

$R^3$ is selected from the group consisting of H and alkyl;

$R^4$ is selected from the group consisting of H, alkyl, alkylcarbonyl, and a counterion; and $R^5$ is selected from the group consisting of H, alkyl, alkylcarbonyl, and a counterion.

In certain embodiments, $R^{1a}$ and $R^{1b}$ are each independently selected from H, alkylcarbonyloxyalkyl, and counterion. In certain embodiments, $R^{1a}$ and $R^{1b}$ are each independently selected from H, alkylcarbonyloxymethyl, and counterion. In certain embodiments, $R^{1a}$ and $R^{1b}$ are each acetoxymethyl.

In certain embodiments, $R^2$ is selected from the group consisting of H, alkyl, acetate, and a counterion. In certain embodiments, $R^2$ is methyl.

In certain embodiments, $R^3$ is H.

In certain embodiments, $R^4$ is selected from the group consisting of H, alkylcarbonyl, and a counterion. In certain embodiments, $R^4$ is acetate.

In certain embodiments, $R^5$ is selected from the group consisting of H, alkylcarbonyl, and a counterion. In certain embodiments, $R^5$ is acetate.

In certain embodiments, $R^2$ is alkyl; $R^3$ is H or alkyl; $R^4$ is alkylcarbonyl; $R^5$ is alkylcarbonyl; and $R^{1a}$ and $R^{1b}$ are each alkylcarbonyloxyalkyl.

In certain embodiments, $R^2$ is $C_1$-$C_6$-alkyl; $R^3$ is H or $C_1$-$C_6$-alkyl; $R^4$ is $C_1$-$C_6$-alkylcarbonyl; $R^5$ is $C_1$-$C_6$-alkylcarbonyl; and $R^{1a}$ and $R^{1b}$ are each $C_1$-$C_6$-alkylcarbonyloxy-$C_1$-$C_6$-alkyl.

In certain embodiments, $R^2$ is methyl; $R^3$ is H; $R^4$ is methylcarbonyl; $R^5$ is methylcarbonyl; and $R^{1a}$ and $R^{1b}$ are each methylcarbonyloxymethyl.

In another aspect, disclosed is a compound of formula (I-a),

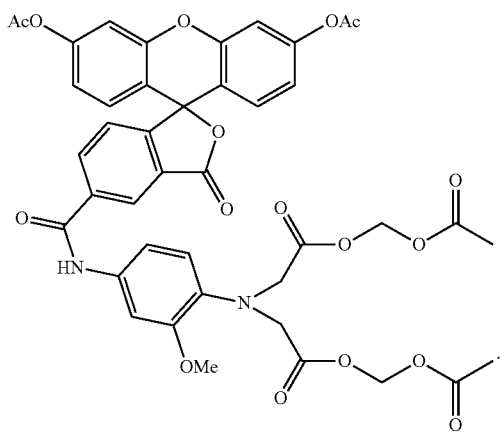

(I-a)

In another aspect, disclosed is a method for detecting the activity of an ion channel in a membrane (e.g., a cell membrane, a planar lipid bilayer, or a liposome). In certain embodiments, the method comprises: providing a cell with an ion channel; providing a loading buffer solution to the cell, the loading buffer solution comprising a non-halogenated fluorescent thallium ion indicator of formula (I), as described above; providing a stimulus buffer to the cell, wherein the stimulus buffer comprises thallium, and wherein providing the stimulus buffer causes thallium influx into the cell through the ion channel; and detecting the thallium indicator. The method may be performed without conducting a wash step.

In another aspect, disclosed is an assay kit for detecting the activity of an ion channel in a membrane (e.g., a cell membrane, a planar lipid bilayer, or a liposome). In certain embodiments, the kit comprises: a thallium loading solution, wherein the solution comprises thallium; and a loading buffer solution, wherein the loading buffer solution comprises a non-halogenated fluorescent thallium indicator of formula (I), as described above. In certain embodiments, the thallium concentration in the loading solution is about 0.1 mM to about 4 mM.

The compounds, compositions, methods, kits and processes are further described herein.

DETAILED DESCRIPTION

Figure 1:
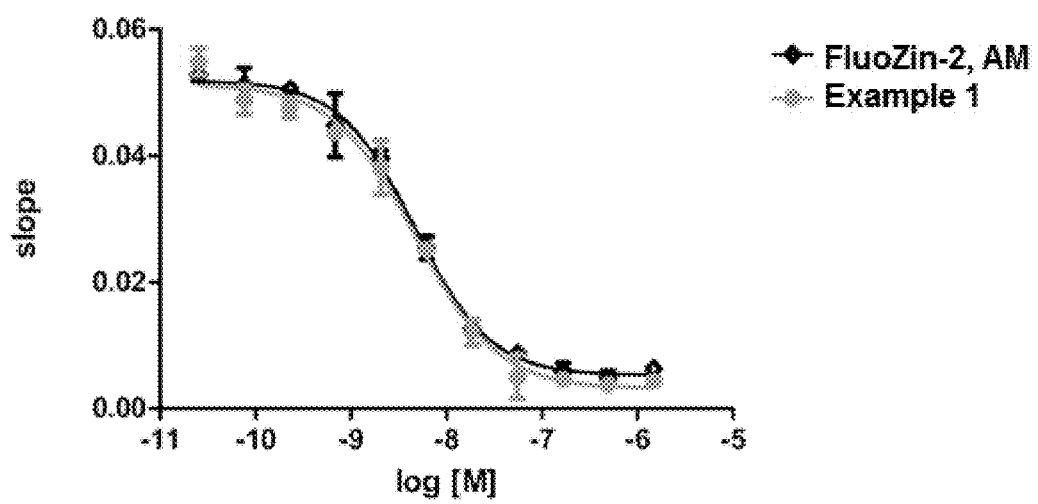
FIG. 1 depicts fluorescence performance of a compound of this disclosure compared to FluoZin-2 fluorescent ion indicator, in an example "wash" test.

Disclosed herein are non-halogenated thallium ion indicators, compositions comprising the indicators, and methods of making and using the indicators. The indicators may be used to detect the activity of an ion channel in a membrane (e.g., a cell membrane, a planar lipid bilayer, or a liposome).

The disclosed thallium ion indicators provide several advantages over currently available indicators and methods. As one advantage, the disclosed non-halogenated thallium ion indicators provide an unexpected improvement in the fluorescence signal-to-background ratio in cell-based assays. In particular, it has been found that the disclosed thallium ion indicators, despite a lack of halogen substituents, exhibit superior signal-to-background fluorescence compared to halogenated xanthene-based indicators, including the current market standard indicator FluxOR™ reagent.

The improved signal-to-background ratio of the disclosed compounds allows for their use in "no-wash" assays. In general, cell-based assays using thallium ion indicators require buffers that must be essentially free of chloride to prevent TlCl from precipitating out of solution during the experiment. Methods involving previously known indicators, therefore, require additional steps of washing and removal of buffers in which cells are normally grown in culture (e.g., chloride containing buffers). Because chloride is absent in these assays, the assays can be seen as not approximating physiological conditions. The presently disclosed thallium ion indicators and assays, due to the improved signal-to-noise ratio, obviate the additional wash steps required by previous methods. Consequently the disclosed indicators and assays allow for efficient, high-throughput screening experiments.

DEFINITION OF TERMS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present disclosure. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," "a," "an" "the" and variants thereof, as used herein, are intended to be open-ended transitional phrases, terms, or words that do not preclude the possibility of additional acts or structures. The present disclosure also contemplates other embodiments "comprising," "consisting of" and "consisting essentially of," the embodiments or elements presented herein, whether explicitly set forth or not.

As used herein, the term "about", when used to describe a numerical value, shall encompass a range up to +/−15% of that numerical value, unless the context clearly dictates otherwise.

As used herein, the term "suitable substituent" is intended to mean a chemically acceptable functional group e.g., a moiety that does not negate the activity (e.g., fluorescence) of the inventive compounds. Illustrative examples of suitable substituents include, but are not limited to alkyl groups, alkenyl groups, alkynyl groups, hydroxy groups, oxo groups, mercapto groups, alkylthio groups, alkoxy groups, aryl or heteroaryl groups, aryloxy or heteroaryloxy groups, aralkyl or heteroaralkyl groups, aralkoxy or heteroaralkoxy groups, HO—(C═O)— groups, heterocylic groups, cycloalkyl groups, amino groups, alkyl—and dialkylamino groups, carbamoyl groups, alkylcarbonyl groups, alkoxycarbonyl groups, alkylaminocarbonyl groups, dialkylamino carbonyl groups, arylcarbonyl groups, aryloxycarbonyl groups, alkylsulfonyl groups, arylsulfonyl groups and the like. Those skilled in the art will appreciate that many substituents can be substituted by additional substituents.

As used herein, the term "alkenyl" refers a straight or branched hydrocarbon chain containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl. Alkenyl groups of the present disclosure may be unsubstituted or substituted by one or more suitable substituents, preferably 1 to 3 suitable substituents, as defined above.

As used herein, the term "alkoxy" refers to an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

As used herein, the term "alkoxyalkyl" refers to an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

As used herein, the term "alkoxycarbonyl" refers to an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

As used herein, the term "alkyl" refers to a linear or branched hydrocarbon radical having the specified number of carbon atoms. The term "$C_1$-$C_6$-alkyl" is defined to include alkyl groups having 1, 2, 3, 4, 5, or 6 carbons in a linear or branched arrangement. For example, "$C_1$-$C_6$-alkyl" specifically includes methyl, ethyl, n-propyl, i-propyl, n-butyl, t-butyl, i-butyl, pentyl, and hexyl. Alkyl groups of the present disclosure may be unsubstituted or substituted by one or more suitable substituents, preferably 1 to 3 suitable substituents, as defined above.

As used herein, the term "alkylamino" refers to an alkyl group, as defined herein, appended to the parent molecular moiety through an amino group, as defined herein. Representative examples of alkylamino include, but are not limited to, methylamino, ethylamino, and sec-butylamino.

As used herein, the term "alkylaminoalkyl" refers to an alkyl group, as defined herein, appended to the parent molecular moiety through an aminoalkyl group, as defined herein. Representative examples of alkylaminoalkyl groups include, but are not limited to, methylaminoethyl and methylamino-2-propyl.

As used herein, the term "alkylcarbonyl" refers to an alkyl group appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

As used herein, the term "alkylcarbonyloxy" refers to an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy.

As used herein, the term "alkylcarbonyloxyalkyl" refers to an alkylcarbonyloxy group, as defined herein, appended to the parent molecular moiety through an alkyl group, as defined herein. Representative examples of alkylcarbonyloxyalkyl include, but are not limited to, acetoxymethyl.

As used herein, the term "alkynyl" refers to a straight or branched hydrocarbon radical having 2, 3, 4, 5, 6, 7, 8, 9 or 10 carbons, and having one or more carbon-carbon triple bonds. Alkynyl groups of the present disclosure include, but are not limited to, ethynyl, propynyl, and butynyl. Alkynyl groups of the present disclosure may be unsubstituted or substituted by one or more suitable substituents, preferably 1 to 3 suitable substituents, as defined above.

As used herein, the term "amino" refers to an —$NH_2$ group.

As used herein, the term "aminoalkyl" refers to at least one amino group, as defined herein, appended to the parent molecular moiety through an alkyl group, as defined herein. Representative examples of aminoalkyl include, but are not limited to, aminomethyl, 2-aminoethyl, and 2-aminopropyl.

As used herein, the term "carbonyl" or "(C=O)" (as used in phrases such as alkylcarbonyl, alkyl —(C=O)— or alkoxycarbonyl) refers to the joinder of the >C=O moiety to a second moiety such as an alkyl or amino group (i.e. an amido group). Alkoxycarbonylamino (i.e. alkoxy(C=O)—NH—) refers to an alkyl carbamate group. The carbonyl group is also equivalently defined herein as (C=O). Alkylcarbonylamino refers to groups such as acetamide.

As used herein, the term "cell" is broadly defined to include synthetic liposomes, lipid bilayers separating two chambers or lipid vesicles from natural sources (e.g. synaptosomal vesicals). The term "cell" is broadly defined to include ionophores and membranes that have been compromised by cells death/dying. The term "cell" is intended to mean one or more cells.

As used herein, the term "counterion" refers to a positively charged ion that is chemically associated with the parent molecular moiety, usually, but not necessarily, by ionic bonding. Representative examples of a counterion include, but are not limited to, $Na^+$, $K^+$, and $NMe_4^+$.

As used herein, the term "di(alkyl)amino" refers to two independently selected alkyl groups, as defined herein, appended to the parent molecular moiety through an amino group, as defined herein. Representative examples of di(alkyl)amino include, but are not limited to, N,N-dimethylamino, N-ethyl-N-methylamino, and N-isopropyl-N-methylamino.

As used herein, the term "di(alkyl)aminoalkyl" refers to a di(alkyl)amino group, as defined herein, appended to the parent molecular moiety through an alkyl group, as defined herein. Representative examples of di(alkyl)aminoalkyl include, but are not limited to, N,N-dimethylaminoethyl and N,N-methyl(2-propyl)aminoethyl.

As used herein, the term "halogen" or "halo" refers to a fluoro, chloro, bromo or iodo radical.

As used herein, the term "hydroxy" refers to an —OH group.

As used herein, the term "hydroxyalkyl" refers to an alkyl group, as defined herein, substituted by at least one hydroxy group. Representative examples of hydroxyalkyl include, but are not limited to, hydroxymethyl, 2-hydroxyethyl, 3-hydroxypropyl, 2,3-dihydroxypropyl, 2,3-dihydroxypentyl, 4-hydroxybutyl, 2-ethyl-4-hydroxyheptyl, 3,4-dihydroxybutyl, and 5-hydroxypentyl.

As used herein, the term "ion channel" includes ion transporters. Examples of ion transporters include, but are not limited to, neurotransmitter ion transporters, e.g., dopamine ion transporter, glutamate ion transporter or serotonin ion transporter, sodium-potassium ATPase, proton-potassium ATPase, sodium/calcium exchanger, potassium-chloride ion co-transporter, and G protein-coupled inwardly-rectifying potassium channels.

As used herein, the term "oxo" refers to a double bonded oxygen (=O) radical wherein the bond partner is a carbon atom. Such a radical can also be thought as a carbonyl group.

A prefix attached to a multi-component substituent only applies to the first component it precedes. To illustrate, the term "alkylcycloalkyl" contains two components: alkyl and cycloalkyl. Thus, the $C_1$-$C_6$-prefix on $C_1$-$C_6$-alkylcycloalkyl means that the alkyl component of the alkylcycloalkyl contains from 1 to 6 carbon atoms; the $C_1$-$C_6$-prefix does not describe the cycloalkyl component. To illustrate further, the prefix "halo" on haloalkoxyalkyl indicates that only the alkoxy component of the alkoxyalkyl substituent is substituted with one or more halogen radicals. If the halogen substitution may only occur on the alkyl component, the substituent would instead be described as "alkoxyhaloalkyl."

A substituent is "substitutable" if it comprises at least one carbon or nitrogen atom that is bonded to one or more hydrogen atoms. Thus, for example, hydrogen, halogen, and cyano do not fall within this definition. In addition, a sulfur atom in a heterocyclyl containing such atom is substitutable with one or two oxo substituents.

If a substituent is described as being "substituted", a non-hydrogen radical is in the place of a hydrogen radical on a carbon or nitrogen of the substituent. Thus, for example, a substituted alkyl substituent is an alkyl substituent in which at least one non-hydrogen radical is in the place of a hydrogen radical on the alkyl substituent. To illustrate, monofluoroalkyl is alkyl substituted with a fluoro radical, and difluoroalkyl is alkyl substituted with two fluoro radicals. It should be recognized that if there is more than one substitution on a substituent, each non-hydrogen radical may be identical or different (unless otherwise stated).

When a substituent is referred to as "unsubstituted" or not referred to as "substituted" or "optionally substituted", it means that the substituent does not have any substituents. If a substituent is described as being "optionally substituted", the substituent may be either (1) not substituted or (2) substituted. If a substituent is described as being optionally substituted with up to a particular number of non-hydrogen radicals, that substituent may be either (1) not substituted; or (2) substituted by up to that particular number of non-hydrogen radicals or by up to the maximum number of substitutable positions on the substituent, whichever is less. Thus, for example, if a substituent is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

If substituents are described as being "independently selected" from a group, each substituent is selected independent of the other. Each substituent, therefore, may be identical to or different from the other substituent(s).

Compounds

Compounds of this disclosure include non-halogenated fluorescent thallium ion indicators. The thallium indicator can exhibit a decrease in fluorescence intensity in the presence of thallium ions or can exhibit an increase in fluorescence in the presence of thallium ions. In certain embodiments, the thallium indicator exhibits a decrease in fluorescence intensity in the presence of thallium ions. In certain embodiments, the thallium indicator exhibits an increase in fluorescence intensity in the presence of thallium ions. Compounds of this disclosure include thallium ion indicators having sensitivity to monovalent ions or divalent ions.

Association of thallium with a compound of this disclosure may occur by any means, with any portion of the compound, and by ionic or non-ionic interaction. In certain embodiments, a compound of this disclosure binds to thallium (I) ions to produce a change in its fluorescence properties.

In some aspects, compounds of this disclosure have formula (I),

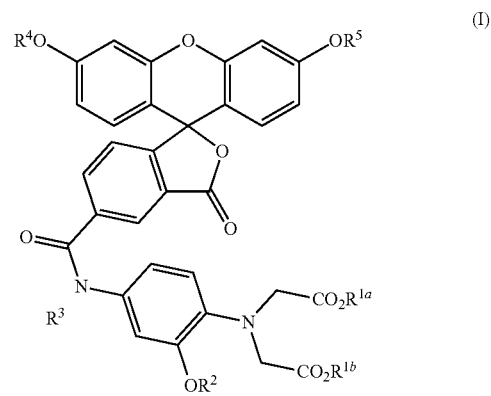

or a salt, ester, or amide thereof,
wherein
$R^{1a}$ and $R^{1b}$ are each independently selected from the group consisting of H, alkyl, hydroxyalkyl, aminoalkyl, alkylaminoalkyl, di(alkyl)aminoalkyl, alkoxyalkyl, alkylcarbonyl, alkoxycarbonyl, alkylcarbonyloxyalkyl, alkenyl, alkynyl, and a counterion;
$R^2$ is selected from the group consisting of H, alkyl, alkylcarbonyl, and a counterion;
$R^3$ is selected from the group consisting of H and alkyl;
$R^4$ is selected from the group consisting of H, alkyl, alkylcarbonyl, and a counterion; and
$R^5$ is selected from the group consisting of H, alkyl, alkylcarbonyl, and a counterion.

In certain embodiments, $R^{1a}$ and $R^{1b}$ are each independently selected from H, alkylcarbonyloxyalkyl, and counterion (e.g., $Na^+$, $K^+$, $NMe_4^+$). In certain embodiments, $R^{1a}$ and $R^{1b}$ are each independently selected from H, alkylcarbonyloxymethyl, and counterion. In certain embodiments, $R^{1a}$ and $R^{1b}$ are each independently selected from H, acetoxymethyl, and counterion. In certain embodiments, $R^{1a}$ and $R^{1b}$ are each acetoxymethyl.

In certain embodiments, $R^2$ is selected from the group consisting of H, alkyl, acetate, and a counterion. In certain embodiments, $R^2$ is selected from the group consisting of H, methyl, acetate, and a counterion. In certain embodiments, $R^2$ is methyl.

In certain embodiments, $R^3$ is selected from the group consisting of H, methyl, ethyl, and propyl. In certain embodiments, $R^3$ is H.

In certain embodiments, $R^4$ is selected from the group consisting of H, alkylcarbonyl, and a counterion (e.g., $Na^+$, $K^+$, $NMe_4^+$). In certain embodiments, $R^4$ is acetate.

In certain embodiments, $R^5$ is selected from the group consisting of H, alkylcarbonyl, and a counterion (e.g., $Na^+$, $K^+$, $NMe_4^+$). In certain embodiments, $R^5$ is acetate.

In certain embodiments, the counterion, at each occurrence, is independently selected from the group consisting of $Na^+$, $K^+$, and $NMe_4^+$.

In certain embodiments, $R^{1a}$ and $R^{1b}$ are each independently selected from the group consisting of H, $C_1$-$C_6$-alkyl, hydroxy-$C_1$-$C_6$-alkyl, amino-$C_1$-$C_6$-alkyl, $C_1$-$C_6$-alkylamino-$C_1$-$C_6$-alkyl, di($C_1$-$C_6$-alkyl)amino-$C_1$-$C_6$-alkyl, $C_1$-$C_6$-alkoxy-$C_1$-$C_6$-alkyl, $C_1$-$C_6$-alkylcarbonyl, $C_1$-$C_6$-alkoxycarbonyl, $C_1$-$C_6$-alkylcarbonyloxy-$C_1$-$C_6$-alkyl, $C_2$-$C_6$-alkenyl, $C_2$-$C_6$-alkynyl, and a counterion; $R^2$ is selected from the group consisting of H, $C_1$-$C_6$-alkyl, $C_1$-$C_6$-alkylcarbonyl, and a counterion; $R^3$ is selected from the group consisting of H and $C_1$-$C_6$-alkyl; $R^4$ is selected from the group consisting of H, $C_1$-$C_6$-alkyl, $C_1$-$C_6$-alkylcarbonyl, and a counterion; and $R^5$ is selected from the group consisting of H, $C_1$-$C_6$-alkyl, $C_1$-$C_6$-alkylcarbonyl, and a counterion.

In certain embodiments, $R^2$ is alkyl; $R^3$ is H or alkyl; $R^4$ is alkylcarbonyl; $R^5$ is alkylcarbonyl; and $R^{1a}$ and $R^{1b}$ are each alkylcarbonyloxyalkyl. In certain embodiments, $R^2$ is $C_1$-$C_6$-alkyl; $R^3$ is H or $C_1$-$C_6$-alkyl; $R^4$ is $C_1$-$C_6$-alkylcarbonyl; $R^5$ is $C_1$-$C_6$-alkylcarbonyl; and $R^{1a}$ and $R^{1b}$ are each $C_1$-$C_6$-alkylcarbonyloxy-$C_1$-$C_6$-alkyl. In certain embodiments, $R^2$ is methyl; $R^3$ is H; $R^4$ is methylcarbonyl (i.e., acetate); $R^5$ is methylcarbonyl; and $R^{1a}$ and $R^{1b}$ are each methylcarbonyloxymethyl (i.e., acetoxymethyl).

In certain embodiments, compounds of this disclosure have formula (I-a),

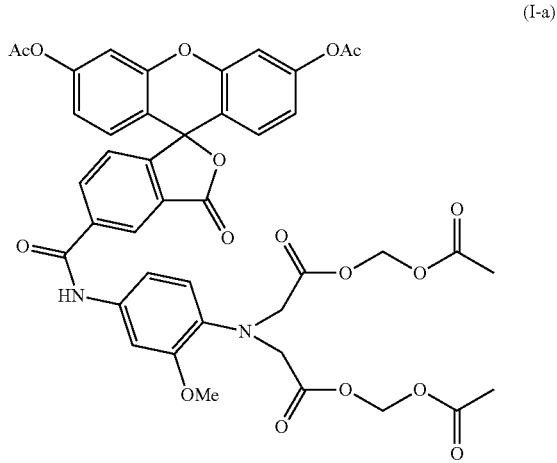 [SMILES: COc1cc(NC(=O)c2ccc3c(c2)C(=O)OC32c3ccc(OC(C)=O)cc3Oc3cc(OC(C)=O)ccc32)ccc1N(CC(=O)OCOC(C)=O)CC(=O)OCOC(C)=O]

(I-a)

or a salt, ester, or amide thereof.

Compounds of this disclosure may contain asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the scope of this disclosure. The present disclosure is meant to comprehend all such isomeric forms of these compounds.

Compounds of this disclosure may include a moiety that increases the hydrophilicity or hydrophobicity of the compound. For example, the compound may be derivatized to convert it to a more hydrophobic form, which may be able to more easily permeate cell membranes. For example, the thallium sensitive fluorescent agents can be loaded into a cell by contacting the cell with a loading buffer comprising the dye or a membrane-permeable derivative of the dye. Loading the cells with the dye may be further facilitated by using a more hydrophobic form of the dye.

For certain applications, it may be desired to provide a thallium indicator with a cleavable hydrophobic moiety. For example, thallium indicators with a cleavable hydrophobic moiety may readily enter the cell through the cell membrane. Once inside the cell, the moiety may be cleaved by an agent (e.g., enzyme) within the cell to produce a less hydrophobic compound, which remains trapped within the cell. The cleavable moiety may be any moiety susceptible to cleavage by an enzyme (e.g., esterases, lipases, phospholipases, and the like).

In certain embodiments, a compound of this disclosure may include an acetoxymethyl ester (AM), which is more hydrophobic in nature than the unmodified form of the dye, and is able to permeate cell membranes much more readily. As the acetoxymethyl ester form of the dye enters the cell, the ester group is removed by cytosolic esterases, thereby trapping the dye in the cytosol.

Compounds of this disclosure may be provided as salts. A "salt" refers to any acceptable salt of a compound, which may be derived from a variety of organic and inorganic counter ions well known in the art and may include, by way of example only, sodium, potassium, calcium, magnesium, ammonium, and tetraalkylammonium; and when the compound contains a basic functionality, salts of organic or inorganic acids, such as hydrochloride, hydrobromide, tartrate, mesylate, acetate, maleate, and oxalate. Representative examples of suitable thallium indicator salts include, but are not limited to, those with a counterion, such as, for example, $Na^+$, $K^+$, $NH^{4+}$, and $NR^{4+}$. Salts of the compounds described herein may be prepared as salts using methods that are well known to those skilled in the art.

Compounds of this disclosure which contain basic nitrogen-containing groups may be quaternized using agents such as ($C_1$-$C_4$)-alkyl halides, for example methyl, ethyl, isopropyl and tert-butyl chloride, bromide and iodide; di($C_1$-$C_4$)alkyl sulfates, for example dimethyl, diethyl and diamyl sulfate; ($C_{10}$-$C_{18}$)alkyl halides, for example decyl, do-decyl, lauryl, myristyl and stearyl chloride, bromide and iodide; and aryl-($C_1$-$C_4$)alkyl halides, for example benzyl chloride and phenethyl bromide.

The acid-addition salts of basic compounds of this disclosure may be prepared by bringing the free base form into contact with a sufficient amount of the desired acid, causing the formation of the salt in a conventional manner. The free base may be regenerated by bringing the salt form into contact with a base and isolating the free base in a conventional manner.

The base-addition salts of acidic compounds of this disclosure may be prepared by bringing the free acid form into contact with a sufficient amount of the desired base, causing the formation of the salt in a conventional manner. The free acid may be regenerated by bringing the salt form into contact with an acid and isolating the free acid in a conventional manner.

If a compound of this disclosure contains more than one group which is capable of forming salts, the compounds of this disclosure also encompasses multiple salts. Typical multiple salt forms include, for example, bitartrate, diacetate, difumarate, dimeglumine, di-phosphate, disodium and trihydrochloride.

Compounds of this disclosure may be prepared in the form of their hydrates. The term "hydrate" includes but is not limited to hemihydrate, monohydrate, dihydrate, trihydrate, tetrahydrate and the like.

Compounds of this disclosure may be prepared in the form of a solvate with any organic or inorganic solvent, for example alcohols such as methanol, ethanol, propanol and isopropanol, ketones such as acetone, aromatic solvents and the like.

Compounds of this disclosure may be prepared in any solid or liquid physical form. For example, the compound may be in a crystalline form, in amorphous form, and have any particle size. Furthermore, the compound particles may be micronized, or may be agglomerated, particulate granules, powders, oils, oily suspensions or any other form of solid or liquid physical form.

Compounds of this disclosure may exhibit polymorphism, and as such, this disclosure provides different polymorphs of the compounds disclosed herein. The term "polymorph" refers to a particular crystalline state of a substance, having particular physical properties such as X-ray diffraction, IR spectra, melting point, and the like.

Synthetic Methods

The compounds of this disclosure can be prepared according to the following illustrative synthetic schemes and methods.

3-oxid hexafluorophosphate ("HATU") and N,N-diisopropylethylamine ("DIPEA") in dimethylformamide ("DMF"), providing a compound of formula (1). Compounds of formula (2) can be prepared, for example, as described below in Scheme 2. Compounds of formula (3) are commercially available (e.g., where $R^4$ and $R^5$ are each methylcarbonyl).

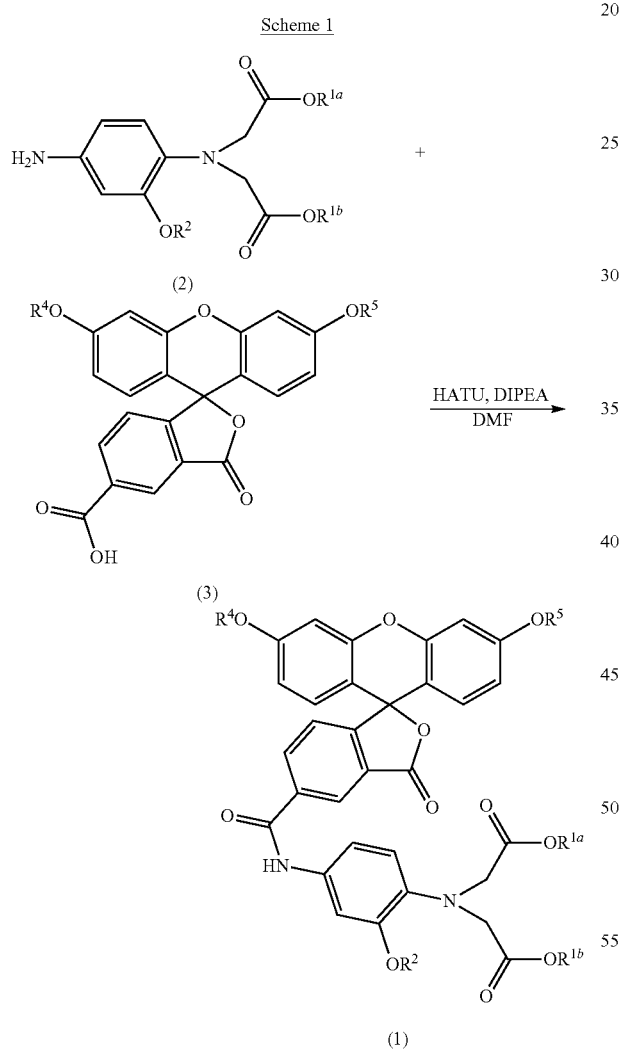

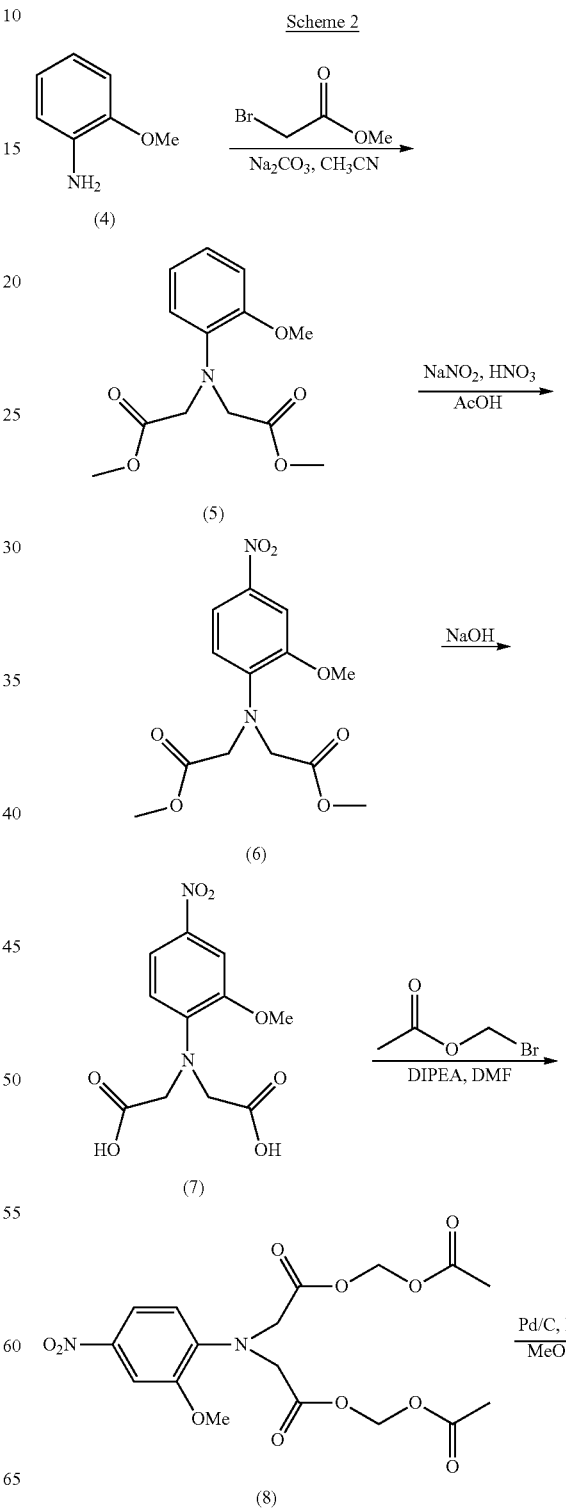

Compounds of formula (1) can be prepared as shown in Scheme 1. A compound of formula (2) can be coupled with a compound of formula (3) by treatment with 1-[bis(dimethylamino)methylene]-1H-1,2,3-triazolo[4,5-b]pyridinium

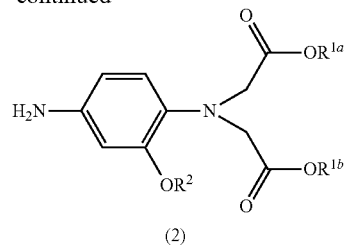

(2)

$R^{1a}, R^{1b} = -CH_2OC(O)CH_3$
$R^2 = Me$

Compounds of formula (2) can be synthesized as shown in Scheme 2. A compound of formula (4) when treated with methyl 2-bromoacetate will provide a compound of formula (5). Treatment of the compound of formula (5) with sodium nitrite and nitric acid will provide a compound of formula (6). Hydrolysis of the methyl esters in the compound of formula (6) can be accomplished by treatment with sodium hydroxide, providing a compound of formula (7). Treatment of the compound of formula (7) with bromomethyl acetate and DIPEA in DMF will provide a compound of formula (8). The nitro functionality of the compound of formula (8) can be reduced to an amino group by treatment with palladium on carbon, hydrogen, and methanol, providing the compound of formula (2).

In certain embodiments, the products may be further modified, for example, by manipulation of substituents. These manipulations may include, but are not limited to, reduction, oxidation, organometallic cross-coupling, alkylation, acylation, and hydrolysis reactions which are commonly known to those skilled in the art. In some cases, the order of carrying out the foregoing reaction schemes may be varied to facilitate the reaction or to avoid unwanted reaction products.

Methods of Use

The fluorescent ion indicators of this disclosure may be used for detecting the activity of an ion channel in a membrane (e.g., a cell membrane, a planar lipid bilayer, or a liposome). Methods to determine activity of an ion channel (e.g., in a cell) may include detecting influx or efflux of thallium ions through an ion channel.

In general, the methods comprise providing a loading buffer solution to the cell, with the loading buffer comprising at least one environmentally sensitive fluorescent thallium indicator [e.g., a compound of formula (I)], and providing a stimulus buffer to the cell, wherein the stimulus buffer comprises thallium. Providing the stimulus buffer can cause thallium influx into the cell through the ion channel. After providing the stimulus buffer, the fluorescence of the indicator (also referred to as a "dye") in the cell is detected, where the fluorescence of the dye can change in the presence or absence of thallium. A combination of two or more thallium indicators may be used in the methods of this disclosure.

A method for detecting the activity of an ion channel in a cell may include a) contacting a cell with a loading buffer solution, wherein the cell comprises an ion channel, and wherein the loading buffer solution comprises an improved thallium indicator, such as a compound of formula (I); b) providing a stimulus buffer to the cell, wherein the stimulus buffer comprises thallium, and wherein providing the stimulus buffer causes thallium influx into the cell through the ion channel; and c) detecting the thallium indicator. In one example, these steps may be conducted in a "no-wash" protocol.

In certain embodiments, the method may further include washing the cells to remove excess thallium. The cells may, optionally, be washed after the loading buffer solution is provided to the cells (e.g., to remove excess thallium indicator). In certain embodiments, the cells are not washed, and a quencher may be added to the loading buffer solution. In these cases, the quencher may be substantially not cell permeant. Examples of quenchers may include, but are not limited to, tartrazine, amaranth, acid red 37, congo red, trypan blue, brilliant black, Red 40 or any combination of these quenchers. In some embodiments, the cells may not be washed and a quencher may not be added. In some embodiments, an anion transport inhibitor may be used to promote dye retention.

Ion Channels and Receptors

The methods of this disclosure may be used to analyze various types of ion channels, including potassium ion channels and sodium ion channels, ion channels that are linked to receptors, channel-linked receptors, and ion transporters. The ion channel may be a ligand- or voltage-gated ion channel, a stretch-activated cation channel, or a selective or non-selective cation channel. The methods are not limited to a particular type of ion channel or transporter, provided that the channel or transporter is permeable to thallium. Examples of ion channels include, but are not limited to, potassium ion channels and/or sodium ion channels, ion channels that are linked to receptors, e.g., GIRK, and channel-linked receptors, e.g., GPCR, and ion transporters, e.g., glutamate transporters.

Types of ligand-gated non-selective cation channels may include, but are not limited to, acetylcholine receptors, glutamate receptors such as AMPA, kainate, and NMDA receptors, 5-hydroxytryptamine-gated receptor-channels, ATP-gated (P2X) receptor-channels, nicotinic acetylcholine-gated receptor-channels, vanilloid receptors, ryanodine receptor-channels, cation channels activated in situ by intracellular cAMP, and cation channels activated in situ by intracellular cGMP.

Types of voltage-gated ion channels may include, but are not limited to, $Ca^{2+}$, $K^+$, and Na+ channels. The channels may be expressed exogenously or endogenously. The channels may be stably or transiently expressed in both native and engineered cell lines.

Types of $K^+$ channels may include, but are not limited to, KCNQ1 (KvLOT1), KCNQ2, KCNQ3, KCNQ4, KCNQ5, HERG, KCNE1 (IeK, MinK), Kv1.5, Kir 3.1, Kir 3.2, Kir 3.3, Kir 3.4, Kir 6.2, SUR2A, ROMK1, Kv2.1, Kv1.4, Kv9.9, Kir6, SUR2B, KCNQ2, KCNQ3, GIRK1, GIRK2, GIRK3, GIRK4, h1K1, KCNA1, SUR1, Kv1.3, hERG, intracellular calcium-activated $K^+$ channels, rat brain (BK2); mouse brain (BK1) and the like.

Types of $Na^+$ channels may include, but are not limited to, rat brain I, II and III, human II, NaV1-NaV9, ENaC, ASIC, and the like.

Types of $Ca^{2+}$ channels may include, but are not limited to, human calcium channel and rabbit skeletal muscle.

The methods of this disclosure may also be applied to indirectly measure the activity of channel-linked receptors and signal transduction systems. Channel activity may be modulated from interactions between receptor subunits with ion channels or by changes in the concentrations of messenger molecules such as calcium, lipid metabolites, or cyclic nucleotides which, modulate the ion channel activity.

Accordingly, this disclosure provides methods for monitoring, detecting and/or measuring the activity of intracellular events that are known to cause changes in ion channel permeability. Intracellular activity may include, but is not limited to, protein phosphorylation or de-phosphorylation, up-regulation or down-regulation of transcription, internal calcium influx or efflux, cellular division, cellular apoptosis, receptor dimerization and the like. Thus, the measurement or detection of such intracellular events can also serve as an indirect detection or measure of the ion channels, if so desired.

In addition, G-coupled protein receptors may also be utilized in the methods of this disclosure. Examples of G-coupled protein receptors include, but are not limited to, muscarinic acetylcholine receptors (mAChR), adrenergic receptors, serotonin receptors, dopamine receptors, angiotensin receptors, adenosine receptors, bradykinin receptors, metabotropic excitatory amino acid receptors and the like.

Another type of indirect assay of this disclosure involves determining the activity of receptors which, when activated, result in a change in the level of intracellular cyclic nucleotides, e.g., cAMP, cGMP. For example, activation of some dopamine, serotonin, metabotropic glutamate receptors and muscarinic acetylcholine receptors results in an increase or decrease in the cAMP or cGMP levels of the cytoplasm. Furthermore, some cyclic nucleotide-gated ion channels, e.g., rod photoreceptor cell channels, olfactory neuron channels, and HCN channels are known to be permeable to cations upon activation by binding of cAMP or cGMP. Thus, in accordance with the methods of this disclosure, a change in cytoplasmic ion levels, caused by a change in the amount of cyclic nucleotide activation of photo-receptor, olfactory neuron channels, or HCN channels can be used to determine the function of receptors that cause a change in cAMP or cGMP levels when activated. In some embodiments, a reagent that increases or decreases intracellular nucleotide levels is added to the cell, e.g., forskolin, prior to the addition of a receptor-activating compound. For example, if activation of a receptor is known or suspected to result in a decrease in cyclic nucleotide levels, forskolin, which is known to increase intracellular levels of nucleotide levels, may be added to the cells prior to adding a receptor-activating compound to the cells in the assay.

Cells used for this type of assay may be generated by co-transfection of a host cell with DNA encoding an ion channel, such as HCN2, and DNA encoding a channel-linked receptor which, when activated, cause a change in cyclic nucleotide levels in the cytoplasm.

Receptors for use in methods of this disclosure, include, but are not limited to, muscarinic receptors, neuronal nicotinic acetylcholine receptors, dopamine receptors, and serotonin receptors.

Cell Types

The methods of this disclosure can be practiced on any cell that possesses/expresses an ion channel that is permeable to thallium. The cells may be in any environment, provided that the loading and stimulus buffers can be applied to the cells. In one embodiment, the cell is in an in vitro environment and the methods are performed using well-known cell culture techniques. In a more specific embodiment, the cell is in a cell culture suspension. In another specific embodiment, the cell is in a cell adhesion culture.

The cells may normally possess or express the ion channels, or the ion channels may be introduced into the cells using well-known transfection, transduction and transformation techniques. Methods are provided for assaying cells expressing native levels of ion channel (e.g., non-engineered cells) and for assaying cells that have been modified (e.g., engineered) by the practitioner to include an ion channel.

The methods of this disclosure may be used to analyze various types of cells, including bacterial, yeast, plant, and animal cells (e.g., mammalian cells). The cell may be a neuron, cardiac cell, cancer cell, a smooth muscle cell, or an immortalized cell. The cell may include one or more cation channel such as a potassium ion channel and/or sodium ion channel, non-selective cation channel, or transporter. The ion channel may be permeable to thallium ions.

Examples of animal cells that can be used in the methods of this disclosure include, but are not limited to, insect cells, avian cells, and mammalian cells. Other examples of cells that may be examined using the methods of this disclosure are neurons, cardiac cells, cancer cells, smooth muscle cells, and the like. In certain embodiments, the cells may be immortalized cells.

Loading Buffer

To perform the methods of this disclosure, a loading buffer solution may be provided to the cells. The loading buffers may comprise a non-halogenated indicator [e.g., a compound of formula (I)] where the fluorescence property of the compound changes in response to thallium ion concentrations.

The loading buffer may also include additional components, including, but not limited to, serum albumin, transferrin, L-glutamine, lipids, antibiotics, β-mercaptoethanol, vitamins, minerals, ATP and similar components may be present. The loading buffer may also include at least one inhibitor of organic ion transport. Additional components to improve solubilization of the thallium indicator, such as surfactants, may be included in the loading buffer. One of skill in the art can determine the optimal concentration of minerals, vitamins, ATP, lipids, essential fatty acids, etc., for use in a given culture. Agents used to assist and retain dye loaded into cells may also be used, such as probenecid in a variety of possible formulations, including a water soluble form or a base-soluble form.

The loading buffer may also comprise chloride (e.g., chloride ions). In some embodiments, the loading buffer may comprise a detectable amount of chloride. In some embodiments, the loading buffer may be chloride-free. In some embodiments, the loading buffer may be substantially free of chloride ions (e.g., less than about 2 mM). In some embodiments, the loading buffer may include less than about 1 mM chloride ions. One of the advantages of the present disclosure is to allow the use of chloride in the loading buffer and in the cell media, prior to stimulating the cells with thallium. In general, the source of chloride in buffers is usually from the NaCl or KCl salt, but the chloride can be from any source if present. The chloride, if present in the buffers, e.g., the loading buffer or the washing buffer, can be at virtually any concentration, since the methods of the present disclosure are not dependent upon the absence of chloride. Because chloride ions do not interfere with the assay, buffers containing physiological relevant concentrations of chloride may be used in the practice of the methods of this disclosure. "Physiological relevant concentration" refers to a concentration that is characteristic of or consistent with an organism's healthy or normal functioning.

Loading and washing buffers can contain Cl$^-$ concentrations ranging from near zero up to above 150 mM and the most appropriate concentration can be determined readily be someone skilled in the art.

In certain embodiments, a quencher may be used to remove excess fluorescence from thallium ion indicator that was not loaded. A "quencher," as used herein, refers to a photon-reducing agent, which absorbs energy emitted by the fluorescent thallium indicator without reemitting fluorescence energy. The use of extracellular quencher removes the need to wash unloaded thallium sensitive fluorescent agent from the cells. The extracellular quenchers are generally not cell permeant and may be light absorbing compounds having a fluorescence that can be easily separated from that of the thallium sensitive fluorescent agent. The absorption spectrum of the extracellular quenchers significantly absorbs the emission of the thallium sensitive fluorescent agent. The extracellular quenchers may be of a chemical composition that prevents their passage into the cells, and, generally, the quenchers may be charged or very large compounds. The concentration range for extracellular quenchers may range from micromolar to millimolar concentrations, depending on their light absorbing properties. Types of extracellular quenchers that may be used include, but are not limited to, tartrazine and amaranth, acid red 37, congo red, trypan blue, brilliant black or a mixture of such quenchers. Quenchers are described in the Sigma-Aldrich Handbook of Dyes, Stains, and Indicators (Floyd G. Green, 1990, St. Louis, Mo., USA).

Stimulus Buffer

After the loading buffer is provided to the cells, a stimulus buffer may be added to the cells to stimulate thallium movement into or out of the cells. The stimulus buffer preferably comprises thallium, as described below.

A stimulus buffer includes a solution that activates an ion channel, channel-linked receptor or ion transporter (e.g., agonist). Some ion channels/transporters may be constitutively active and thus would not require a "stimulus" in addition to the thallium ion tracer. For channels that require a stimulus, that stimulus may be ligand—a molecule that binds to the channel or channel linked receptor and activates the same (an agonist). A stimulus may also be a change in membrane potential for voltage-gated channels. Typically voltage-gated channels are activated by either direct electrical stimulation with electrodes or by using a stimulus solution that contains an ionic composition that will cause depolarization or hyperpolarization (such as high external potassium). In addition, thallium ions can also act as a stimulus for voltage-gated channels. In such a case, thallium ions can act as both a "tracer" and a depolarizing stimulus. In an influx assay, thallium ions may be added just before, during, or after the addition of a stimulus.

The methods of the present disclosure may include the use of stimulus buffers that are selected based on the type of ion channel, channel-linked receptor or ion transporter used in the method. In some embodiments, the stimulus buffers may include a buffer that does not include reagents that activate the ion channel, such that the ion channels, the channel-linked receptors or the ion transporters remain substantially at rest. In these embodiments, the stimulus solution may include reagents that do not activate the ion channel, channel-linked receptor or ion transporter of interest but facilitate activation of ion channel, channel-linked receptor or ion transporter when a modulating reagent is added to the cells to initiate the assay.

The stimulus solution selected for use with voltage-dependent ion channels, e.g., the N-type calcium channel or KCNQ2 channel, depends upon the sensitivity of the ion channel to the resting potential of the cell membrane. For methods using these voltage-dependent ion channels, the stimulating solution may include activating reagents that serve to depolarize the membrane, e.g., ionophores, valinomycin, etc. The activating reagents may be Tl+ impermeant.

A stimulus buffer selected for use with some voltage-dependent ion channels for activation by depolarization of the cell membrane may include potassium salt at a concentration such that the final concentration of potassium ions in the cell-containing well is in the range of about 10-150 mM, e.g., 50 mM KCl. In addition, voltage-dependent ion channels may also be stimulated by an electrical or light activated stimulus, such as is the case with light excitation of quantum dot nanocrystals or light sensitive ion channels expressed on the cell's surface.

The stimulus buffer selected for use with channel-linked receptors and ligand-gated ion channels may depend upon ligands that are known to activate such receptors. For example, nicotinic acetylcholine receptors are known to be activated by nicotine or acetylcholine; similarly, muscarinic acetyl choline receptors may be activated by addition of muscarine or carbamylcholine. The stimulating buffer for use with these systems may include nicotine, acetylcholine, muscarine or carbamylcholine. In some embodiments, the stimulus may include an agonist of a G-protein coupled receptor that is capable of activating GIRK potassium ion channels to allow thallium influx. In some embodiments, the stimulus buffer may include a composition that will cause depolarization of the ion channel. A depolarizing composition may include, for example, agents such as ionophores, valinocmycin, or potassium salts. Depolarization of cell membranes may be achieved using light activated ion channels on the cell surface, such as channel rhodopsin or halorhodopsin, or light activated quantum dot nanocrystals, among others.

In certain embodiments, a method of this disclosure may include stimulating the ion channel with a stimulus (e.g., a ligand that binds to the ion channel, a channel-linked receptor, a mechanical, a thermal, an optical, or an electrical stimulus, among others). The stimulus may include a G-protein coupled receptor agonist capable of activating GIRK potassium ion channels to allow thallium influx. Alternatively or additionally, the stimulus may include nicotine, acetylcholine, muscarine, carbamyline, or a GIRK potassium ion channel activator. The stimulus may include a composition that will cause depolarization of the ion channel (e.g., ionophores, valinocmycin, or potassium salts, among others) or a composition that includes channel rhodopsin, halorhodopsin, or quantum dot nanocrystals, among others. In other examples, the ion channel may comprise one or more hyperpolarization activated channels.

The stimulus buffer may include normal Cl$^-$ containing solutions. In certain embodiments, other anions compatible with thallium solubility may be included and/or may replace Cl$^-$. For example, bicarbonate, gluconate, nitrate, sulfate, or the like, may be used as a replacement for Cl$^-$ that may be present in a stimulus buffer. HCO$_3^-$ is a physiologically relevant anion that may be used to replace Cl$^-$ in stimulus buffer with no negative effects on Tl$^+$ solubility. When used in some embodiments, the final Cl/HCO$_3$ concentrations are very close to what is observed in the body. So, from a physiological ion concentration, this may be preferred in some situations.

Thallium Form and Concentration

Thallium in the stimulus buffer may be in any form, such as in the form of a salt that provides thallium ions. In certain embodiments, the source of thallium is a salt. The thallium salts for use in thallium solutions used in the methods of this disclosure may include those that are water soluble, including, but not limited to, Tl$_2$SO$_4$, Tl$_2$CO$_3$, TlCl, TlOH, TlOAc, TlNO$_3$ salts and the like. In certain embodiments, the thallium salt may be soluble in the loading buffer solution.

The thallium in the stimulus buffer may be at a very low concentration, because the thallium indicators of this disclosure are sensitive to very low concentrations of thallium. Because thallium may be present in a low concentration, thallium ions may remain soluble in the buffers described herein, regardless of the concentration of chloride. Generally, the thallium (e.g., thallium ions) in the stimulus buffer may be at a concentration of less than about 4.5 mM. In certain embodiments, the stimulus buffer may include thallium at a concentration between about 0.1 and about 4.5 mM.

In another aspect, solutions are provided that include a thallium indicator, a loading buffer comprising a thallium indicator, and thallium ions. The thallium concentration in the solution may be less than about 4.5 mM, but the solution may include higher concentrations of thallium, as well.

In some examples, the thallium flux may be used in normal, $Cl^-$ containing buffers.

Fluorescent Signal

The transport of thallium sensitive agents and thallium ions into cells may be followed by an increase or decrease in fluorescence signal. Thallium ions move through open channels along their concentration gradient and change the intensity of dye fluorescence inside the cell, resulting in the recorded signals. Activation of the ion channel enhances the rate of influx of thallium ions (resulting in a change in the fluorescence of the thallium sensitive fluorescent compound) and inhibition decreases the rate of influx of thallium ions (resulting in no or little change in the fluorescence of the thallium sensitive fluorescent agent). Generally the fluorescence remains the same if no thallium ion is bound to it.

Any optical property of the fluorescent dyes of this disclosure can be measured or detected to determine thallium influx or efflux. Examples of optical properties of fluorescent dyes include, but are not limited to, intensity, polarity and excitation/emission wavelength of the fluorescence of the fluorescent dyes. The fluorescence of the thallium sensitive agent may be measured by devices that detect fluorescent signals, including, but not limited to, spectrophotometers, microscopes and the like. In some embodiments, the fluorescence of the dyes may be detected and/or measured using a standard plate reader. In some embodiments, flow cytometers, fluorescence microscopy, and other devices and methods may be used to detect fluorescence.

In some embodiments, the activity of channel-linked receptors may be determined, where the activation of the receptor initiates subsequent intracellular events that lead to the modulation of ion channel activity.

Methods for Detecting Efflux

The present disclosure also provides methods for detecting the efflux of thallium through an ion channel. In general, methods to evaluate thallium efflux involve loading a cell that includes an ion channel with thallium using methods that are known to those skilled in the art. For example, a cell may be combined with a buffer containing thallium salt and incubated for a time sufficient to load the cells with thallium. The thallium-loaded cells may, optionally, be washed to remove excess thallium. A solution that includes a thallium indicator then may be added to the cell and the ion channel of the cell may be stimulated, such as to cause flux of thallium through the ion channel. A thallium indicator that is impermeable to the ion channel may be used, such that the indicator does not pass into the cell. Fluorescent detection of the thallium indicator upon stimulation of the cell provides information about the activity of the ion channel.

The efflux assays may use the same cells as in the influx assays, and are loaded with a signal generating thallium sensitive fluorescent agent, as described herein. The cells may be contacted with thallium to load the cells. Some embodiments provide contacting the cells with thallium ions for approximately 15 minutes. In some examples, the cells can be washed to remove excess thallium ions and assayed using the same instrument to detect changes in signal as used in the influx assay, such as a plate reader. The assay channels may be stimulated to open by the addition of any one of a number of ligands, or by changing the membrane potential of the cell, such as by changing the potassium concentrations, to permit efflux of ions through the ion channels. For example, an efflux may result in a decrease in fluorescence of the thallium indicator. The other compounds, such as control compounds, may be the same as used in the influx assays. The same conditions may be applied as for the influx assay in the methods of this disclosure, except the cells may be preloaded with thallium ions as described above, and washed to remove excess thallium ions.

In certain embodiments, a method for detecting the activity of an ion channel in a cell may comprise: a) loading a cell with thallium, wherein the cell comprises an ion channel; b) providing a solution to the cell, the solution comprising a thallium indicator a; c) stimulating the ion channel of the cell, such as to cause efflux of thallium through the ion channel; and d) detecting the thallium indicator. The thallium concentration in the cell after loading may be less than about 4.5 mM. The thallium indicator used in this method may include, but is not limited to, a fluorescent compound comprising a non-halogenated xanthene moiety.

Ion Channel Detection Methods and High Throughput Screening

The methods of the present disclosure may be adapted to high-throughput screening methods, such that candidate ion channel modulators can be screened on a large scale. High-throughput screening assays are known, and employ the use of microtiter plates or pico- nano- or micro-liter arrays.

The high-throughput methods of this disclosure may be performed using whole cells expressing ion channels, ion channel and channel-linked receptors or ion transporters of interest, by practicing the methods of the present disclosure on microtiter plates or the like. The cells may be cultured under adherent or non-adherent conditions. In some embodiments, the target compounds may be added to the cells as a pre-treatment and then the stimulus buffer(s) may be added to the cells and fluorescence may be detected. In some embodiments, the target compounds may be added to the cells along with the stimulus buffer(s). The change in the detectable signal would indicate the effect of the channel modulators in a particular well on a plate.

The assays of this disclosure are designed to permit high throughput screening of large chemical libraries, e.g., by automating the assay steps and providing candidate modulatory compounds from any convenient source to assay. Assays which are run in parallel on a solid support, e.g., microtiter formats on microtiter plates in robotic assays, are well known. Automated systems and methods for detecting and/or measuring changes in optical detection are also well known.

The high throughput screening methods of this disclosure may include providing a combinatorial library containing a large number of potential therapeutic modulating compounds. Preparation and screening of combinatorial chemical libraries is well known to those of skill in the art.

EXEMPLARY EMBODIMENTS

Example assay systems including a culture medium, loading buffer, wash buffer, and/or stimulus buffer may include, but are not limited to:

$Cl^-$ free culture medium, $Cl^-$ free loading buffer, $Cl^-$ free wash buffer, $Cl^-$ free stimulus buffer, washed;

$Cl^-$ free culture medium, $Cl^-$ free loading buffer with probenecid, $Cl^-$ free wash buffer with probenecid, $Cl^-$ free stimulus buffer, washed;

$Cl^-$ free culture medium, $Cl^-$ free loading buffer, $Cl^-$ free stimulus buffer, no wash;

$Cl^-$ free culture medium, $Cl^-$ free loading buffer with probenecid, $Cl^-$ free stimulus buffer, no wash;

Cl⁻ free culture medium, Cl⁻ free loading buffer, Cl⁻ free stimulus buffer, no wash+quencher; and Cl⁻ free culture medium, Cl⁻ free loading buffer with probenecid, Cl⁻ free stimulus buffer, no wash+quencher.

Variations of the example embodiments include, but are not limited to:

Normal Cl⁻ containing culture medium, Cl⁻ free loading buffer, Cl⁻ free stimulus buffer, washed;

Normal Cl⁻ containing culture medium, Cl⁻ containing loading buffer, Cl⁻ containing wash buffer, Cl⁻ free stimulus buffer, washed;

Normal Cl⁻ containing culture medium, Cl⁻ containing loading buffer, Cl⁻ containing wash buffer, Cl⁻ free stimulus buffer, no wash;

Normal Cl⁻ containing culture medium, Cl⁻ containing loading buffer, Cl⁻ containing wash buffer, Cl⁻ containing stimulus buffer, washed; and Normal Cl⁻ containing culture medium, Cl⁻ containing loading buffer, Cl⁻ containing wash buffer, Cl⁻ containing stimulus buffer, no wash.

The use of some of these embodiments may be restricted due to limitations on Tl+ solubility.

Kits

This disclosure also provides kits for conveniently and effectively implementing the methods of this disclosure. Such kits may include any compound or composition of this disclosure, and optionally one or more of instructions, packaging, and dispensers. Kit components may be packaged for either manual or partially or wholly automated practice of the foregoing methods. In some embodiments involving kits, this disclosure contemplates a kit including compositions of the present disclosure, and optionally instructions for their use.

The kit may be an assay kit for detecting thallium influx or efflux activity of an ion channel in a cell. Certain kits for detecting thallium ion influx can include a loading buffer solution, wherein the loading buffer solution comprises a thallium indicator; an anion transport inhibitor; and a stimulus buffer comprising thallium, wherein the stimulus buffer causes thallium influx into the cell through the ion channel. Certain kits for detecting thallium ion efflux may include a thallium loading solution comprising thallium; and a buffer solution that comprises a thallium indicator.

In some embodiments, the kits may include a compound of this disclosure (also referred to herein as a "dye"), an assay buffer, and a stimulus buffer. The individual components of the buffers and the dyes may be lyophilized or stored in some other dehydrated form, where an individual may dissolve or solubilize the components into stock or working solutions. The kits may contain virtually any combination of the components set out above or described elsewhere herein.

Some exemplary kits for detecting the thallium influx activity of an ion channel in a cell may include: a) a loading buffer solution that includes a thallium indicator; and b) a stimulus buffer that includes thallium, wherein the stimulus buffer causes thallium influx into the cell through the ion channel. Some exemplary kits for detecting the thallium efflux activity of an ion channel in a cell may include: a) a thallium loading solution that includes thallium ions; and b) a buffer solution that includes a thallium indicator. The components supplied with kits of this disclosure may vary with the intended use for the kits. Thus, kits may be designed to perform various functions set out in this application and the components of such kits may vary accordingly.

EXAMPLES

The following examples are given for illustrative purposes only, and shall not be construed as being a limitation on the scope of the claims.

Example 1 bis(acetoxymethyl) 2,2'-((4-(3',6'-diacetoxy-3-oxo-3H-spiro[isobenzofuran-1,9'-xanthen]-5-ylcarboxamido)-2-methoxyphenyl)azanediyl)diacetate

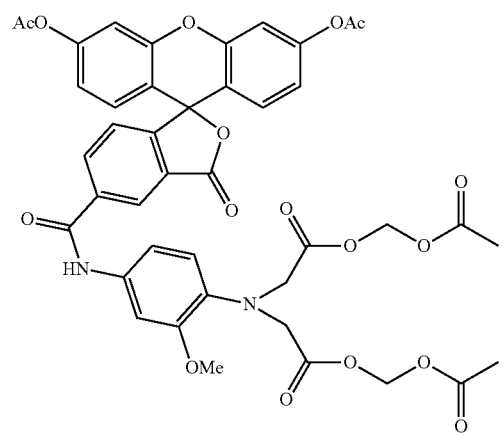 [SMILES: COc1cc(NC(=O)c2ccc3c(c2)C(=O)OC32c3ccc(OC(C)=O)cc3Oc3cc(OC(C)=O)ccc32)ccc1N(CC(=O)OCOC(C)=O)CC(=O)OCOC(C)=O]

Example 1A

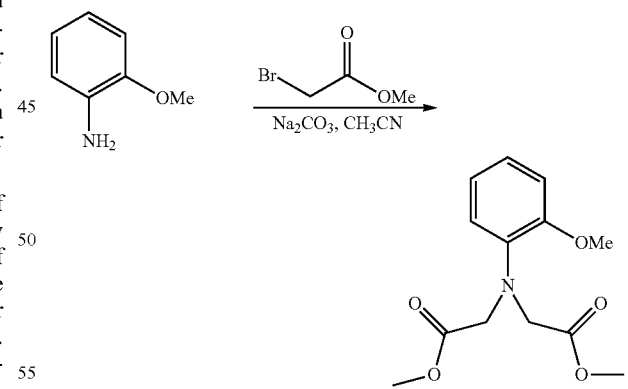

To a solution of 2-methoxyaniline (1.0 g, 8.12 mmol) and methyl-2-bromoacetate (2.31 mL, 24.4 mmol) in acetonitrile (27 mL) was added sodium carbonate (3.44 g, 32.5 mmol). The reaction mixture was stirred overnight under reflux conditions, then filtered through a Celite pad and the filtrate concentrated in vacuo. The residue was purified by column chromatography using Hex/EtOAc (gradient: 0 to 50% EtOAc) to afford dimethyl 2,2'-((2-methoxyphenyl)azanediyl)diacetate (1.98 g, 92%) as an oil. $^1$H NMR (CDCl$_3$, 400 MHz) δ (ppm) 6.97-6.91 (m, 1H), 6.87-6.81 (m, 3H), 4.15 (s, 4H), 3.80 (s, 3H), 3.72 (s, 6H); LCMS (ESI) tR: 0.642 min (>99%, ELSD), m/z: 268.0 [M+1]+.

Example 1B

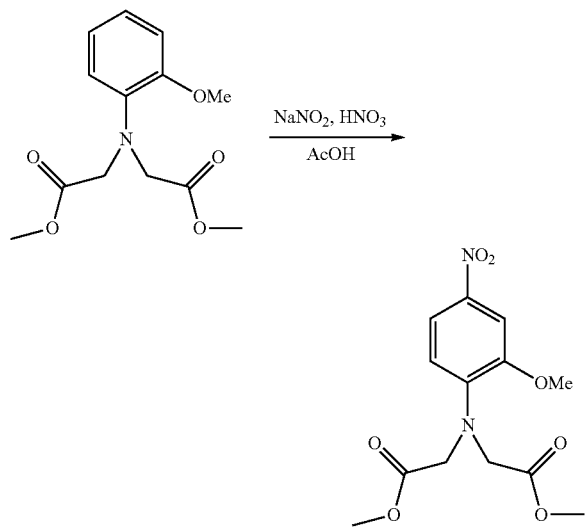

Dimethyl 2,2'-((2-methoxyphenyl) azanediyl)diacetate (1.98 g, 7.41 mmol) was dissolved in acetic acid (10 mL) at room temperature followed by sodium nitrite (51 mg, 0.74 mmol). The nitric acid (0.49 mL, 8.15 mmol) was added dropwise to reaction mixture. After stirring 1 h, the reaction mixture was poured into water (20 mL), extracted with ethyl acetate (20 ml×3), and dried over MgSO$_4$. The residue was purified by column chromatography using Hex/EtOAc (gradient: 0 to 50% EtOAc) to afford dimethyl 2,2'-((2-methoxy-4-nitrophenyl)azanediyl)diacetate (1.98 g, 86%) as a yellow oil. $^1$H NMR (CDCl$_3$, 400 MHz) δ (ppm) 7.80 (dd, J=8.8, 2.4 Hz, 1H), 7.69 (d, J=2.4 Hz, 1H), 6.66 (d, J=8.8 Hz, 1H), 4.20 (s, 4H), 3.85 (s, 3H), 3.78 (s, 6H); LCMS (ESI) tR: 0.678 min (>99%, ELSD), m/z: 313.2 [M+1]+

Example 1C

Example 1C

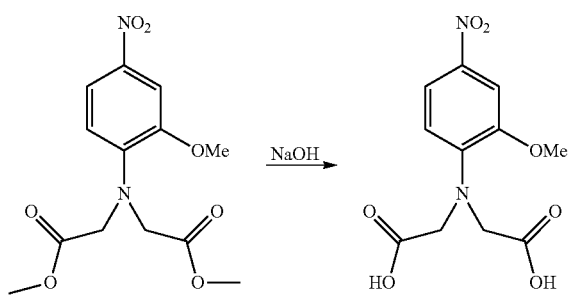

To a solution of the diacetate of Example 1B (1.98 g, 6.34 mmol) in MeOH/1,4-dioxane (12/24 mL) was added NaOH (12 mL, 2 M solution) and then stirred for 1 h at room temperature. The reaction mixture was neutralized with aqueous HCl (1 N solution) and filtered to provide a yellow solid product (1.47 g, 82%); LCMS (ESI) tR: 0.474 min (>99%, ELSD), m/z: 285.1 [M+1]+

Example 1D

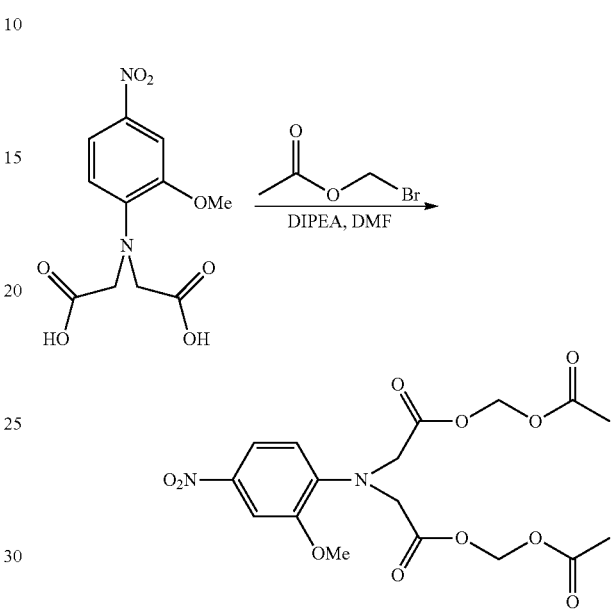

To a solution of dicarboxylic acid of Example 1C (0.72 g, 2.50 mmol) in DMF (10 mL) at 0° C. was added DIPEA (3.05 mL, 17.5 mmol) followed by bromomethyl acetate (0.98 mL, 10.0 mmol). The reaction mixture was allowed to warm to room temperature and stirred for 2 h. The mixture was then concentrated in vacuo and the residue was purified by column chromatography using Hex/EtOAc (gradient: 0 to 50% EtOAc) to afford the bis-acetoxymethyl diacetate product (0.74 g, 68%) as a yellow oil. $^1$H NMR (CDCl$_3$, 400 MHz) δ (ppm) 7.79 (dd, J=8.8, 2.4 Hz, 1H), 7.69 (d, J=2.4 Hz, 1H), 6.65 (d, J=8.8 Hz, 1H), 5.81 (s, 4H), 4.22 (s, 4H), 3.85 (s, 3H), 2.12 (s, 6H); $^{13}$C NMR (CDCl$_3$, 100 MHz) δ 169.4, 169.3, 149.6, 144.4, 141.5, 117.9, 115.9, 107.4, 79.6, 56.0, 54.0, 20.6; LCMS (ESI) tR: 0.723 min (>99%, ELSD), m/z: 429.1 [M+1]+

Example 1E

Example 1E

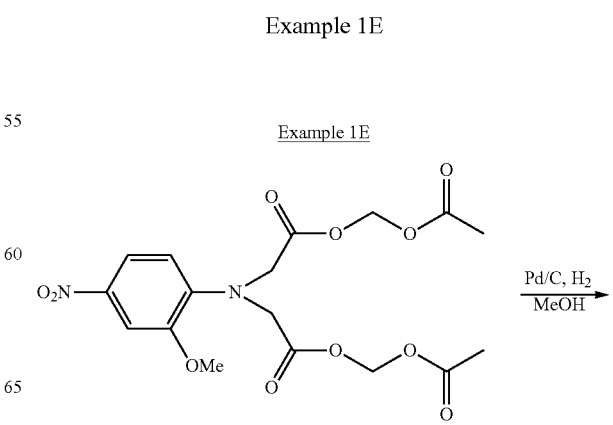

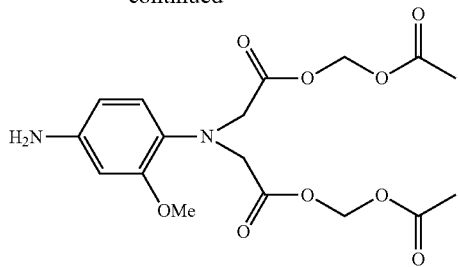

A solution of the diacetate product of Example 1D (0.70 g, 1.63 mmol) in EtOH (5.5 mL) was slowly added to a slurry of 10% Pd/C in MeOH under an atmosphere of argon. The resulting suspension was hydrogenated using a balloon for 16 h. The reaction solution was passed through a Celite pad and the filtrate concentrated in vacuo to afford the aminobenzene product (578 mg, 89%) as a brown oil of sufficient purity to be used without further purification. $^1$H NMR (MeOD, 400 MHz) δ (ppm) 6.72 (d, J=8.4 Hz, 1H), 6.38 (d, J=2.4 Hz, 1H), 6.21 (dd, J=8.4, 2.4 Hz, 1H), 5.72 (s, 4H), 4.01 (s, 4H), 3.75 (s, 3H), 2.05 (s, 6H); LCMS (ESI) tR: 0.513 min (>99%, ELSD), m/z: 399.2 [M+1]+

Example 1F

To a solution of commercially available 5-carboxyfluorescein diacetate (174 mg, 0.43 mmol) in DMF (4 mL) at 0° C. was added DIPEA (0.26 mL, 1.52 mmol) followed by HATU (198 mg, 0.52 mmol). After stirring 30 min at 0° C., the aminobenzene product of Example 1E (200 mg, 0.43 mmol) was added to the reaction mixture and stirred for 2 h at room temperature. The mixture was then poured into water and resulting orange solid was filtered off. The residue was purified by column chromatography using Hex/EtOAc (gradient: 0 to 100% EtOAc with 1% of triethylamine) to afford the desired amide product (110 mg, 30%) as a white solid: $^1$H NMR (CDCl$_3$, 400 MHz) δ (ppm) 8.19-8.06 (m, 3H), 7.57 (s, 1H), 7.34 (s, 1H), 7.04 (s, 2H), 6.86 (dd, J=8.8, 1.6 Hz, 1H), 6.81-6.73 (m, 5H), 5.75 (s, 4H), 4.13 (s, 4H), 3.72 (s, 3H), 2.32 (s, 6H), 2.08 (s, 6H); $^{13}$C NMR (CDCl$_3$, 100 MHz) δ 170.0, 169.4, 169.1, 167.9, 163.2, 153.0, 152.1, 151.5, 151.2, 141.3, 135.0, 132.9, 129.8, 128.8, 128.2, 125.6, 122.1, 119.4, 117.9, 115.6, 112.5, 110.5, 105.1, 81.6, 79.2, 55.4, 53.5, 21.0, 20.6; LCMS (ESI) tR: 0.856 min (>99%, ELSD), m/z: 841.2 [M+1]+

Assay Performance

Figure 2:
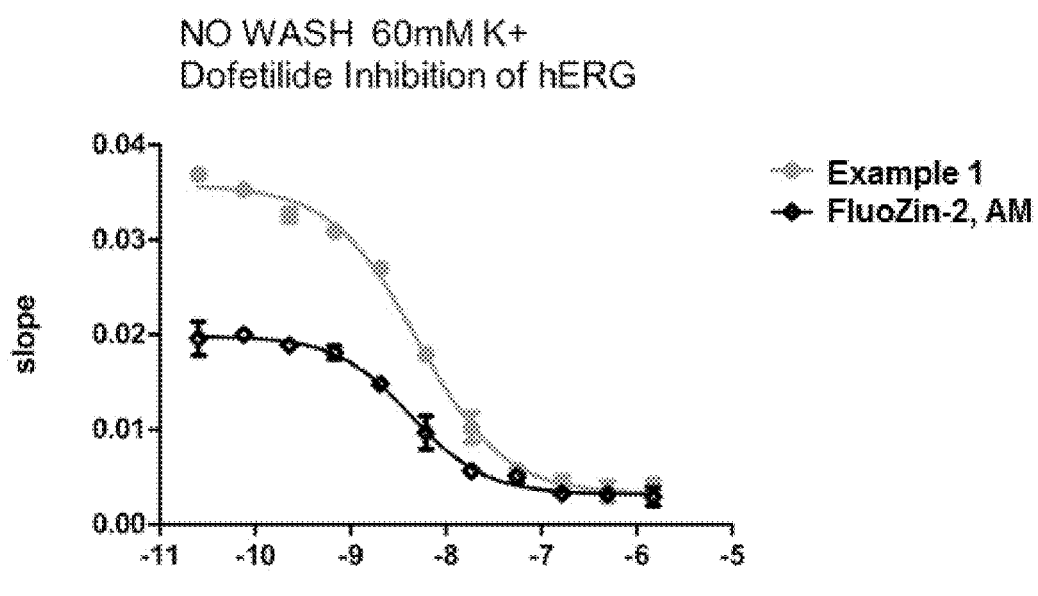
FIG. 2 depicts fluorescence performance of a compound of this disclosure compared to FluoZin-2 fluorescent ion indicator, in an example "no-wash" test.

FIGS. 1 and 2 show results for "Wash" and "No-wash" protocols for the compound of Example 1 compared to the known indicator compound referred to herein as "FluoZin-2, AM." The fluorescence results for the indicators are essentially indistinguishable for the "wash" protocol (FIG. 1), but the compound of Example 1 showed substantial and unexpected improvement in normalized signal amplitude over FluoZin-2, AM in the "no-wash" protocol (FIG. 2).

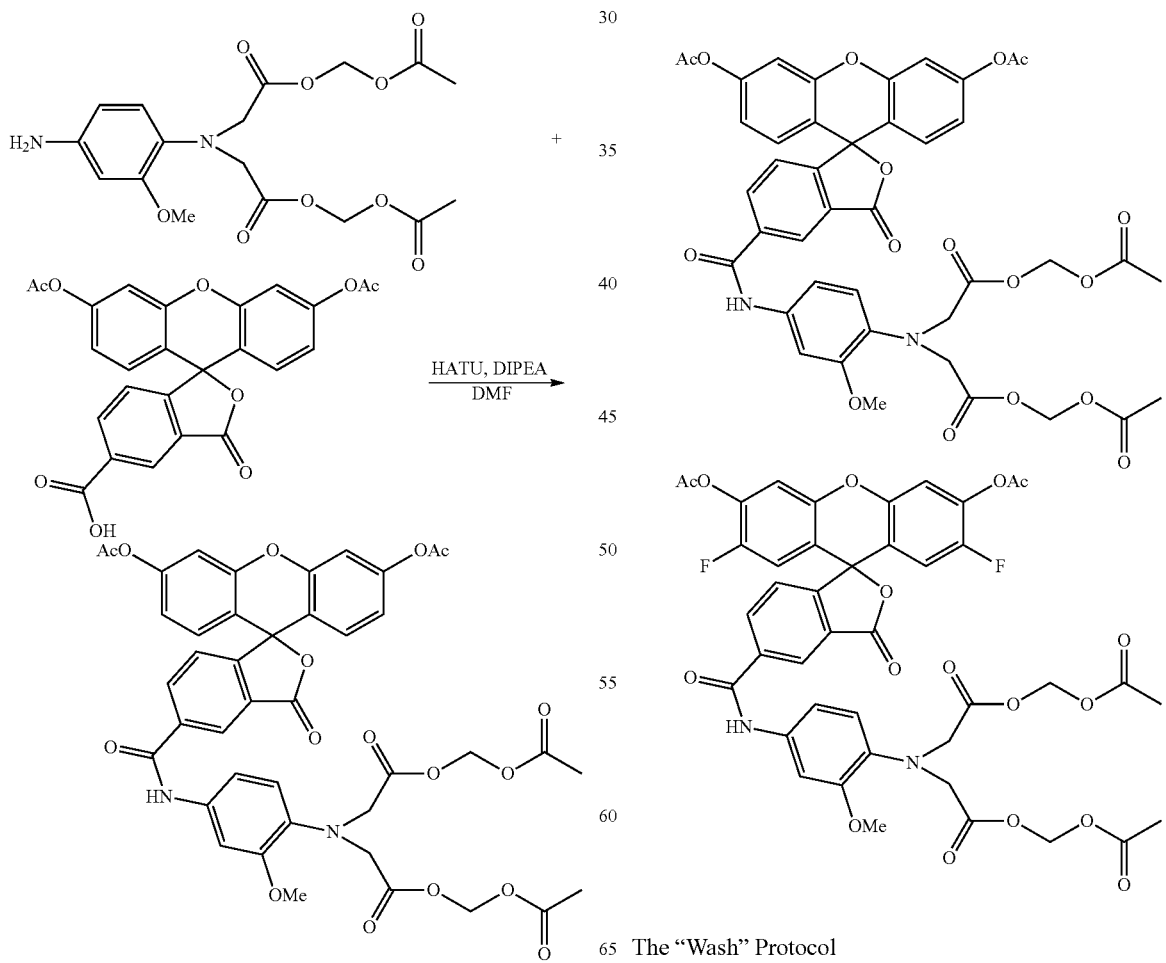

The "Wash" Protocol

The wash protocol experiment was conducted as follows. To a 384-well, black-wall, clear bottom, poly-D-lysine coated plate, add 20 μl/well of α-MEM containing 10% fetal bovine serum and 1× glutaGRO (Cell Culture Medium) and a 1000 cell/μl suspension of HEK-293 cells stably transfected with hERG potassium channels (Cell Plate). Incubate the Cell Plate overnight in a 5% $CO_2$ cell culture incubator at 37° C. Remove the Cell Culture Medium from the Cell Plate and replace it with 20 μl/well Hanks Balanced Salt Solution+20 mM HEPES pH 7.3 (Assay Buffer). Dissolve 25 μg of thallium ion indicator (also referred to as a "dye") in 25 μl DMSO containing 7% (w/v) Pluronic F-127. Add 12.5 μl of the dissolved thallium ion indicator to 10 ml Assay Buffer (Dye Loading Solution). Add 20 μl/well of Dye Loading Solution to the Cell Plate. Incubate the Cell Plate containing Dye Loading Solution for 1 hour at room temperature. Prepare a 384-well, polypropylene plate containing 40 μl/well of Assay Buffer where 60 mM potassium replaces 60 mM of the sodium in the buffer (60 K Assay Buffer) containing a range of concentrations of dofetilide, a known hERG inhibitor (Compound Plate). Remove Dye Loading Solution from the Cell Plate and replace it with 20 μl/well 60 K Assay Buffer (Dye Loaded Cell Plate). Transfer 20 μl/well of samples from the Compound Plate to the Dye Loaded Cell Plate (Compound Treated Cell Plate). Incubate the Compound Treated Cell Plate for 20 minute at room temperature. Prepare a Stimulus Plate using a 384-well, polypropylene plate containing 40 μl/well of a buffer containing 125 mM sodium gluconate, 2.4 mM thallium sulfate, 1 mM magnesium sulfate, 1.8 mM calcium gluconate, 5 mM glucose, 10 mM HEPES, pH 7.3. (Stimulus Buffer). Transfer both the Compound Treated Cell Plate and the Stimulus Plate to a Hamamatsu FDSS or the like and execute a Data Acquisition Protocol where images of the Compound Treated Cell Plate are acquired every 1 second with an excitation wavelength of 470±20 nm, and an emission wavelength of 540±20 nm. Acquire images for 10 seconds. At the 10 second time point during image acquisition, transfer 10 μl/well from the Stimulus Plate to the Compound Treated Cell Plate using the FDSS's internal pippettor to initiate thallium flux. Acquire images every 1 second with an excitation wavelength of 470±20 nm, and an emission wavelength of 540±20 nm for an additional 110 seconds. Analyze data representing the amplitude of the fluorescent signal for each well at each of the 120 time points acquired during the Data Acquisition Protocol using Microsoft Excel by first dividing the fluorescence values from each individual well at each time point by the fluorescent value for that well at the first time point (Normalized Fluorescence Values). Calculate slopes of the Normalized Fluorescence Values between the 12 second and 22 second time points (Slope Values). Average Slope Values from each of four wells containing the same concentration of dofetilide to arrive at Mean Slope Values for each dofetilide concentration. Calculate standard errors of the mean (SEM) for the corresponding data points. Fit Mean Slope Values to a four-parameter logistic equation using GraphPad Prism. Plot the Mean Slope Values+/−SEM and fits as shown in FIG. 1.

The "No-Wash" Protocol

The no-wash protocol was conducted as follows. To a 384-well, black-wall, clear bottom, poly-D-lysine coated plate, add 20 μl/well of α-MEM containing 10% fetal bovine serum and 1× glutaGRO (Cell Culture Medium) and a 1000 cell/μl suspension of HEK-293 cells stably transfected with hERG potassium channels (Cell Plate). Incubate the Cell Plate overnight in a 5% $CO_2$ cell culture incubator at 37° C. Remove the Cell Culture Medium from the Cell Plate and replace it with 20 μl/well Hanks Balanced Salt Solution+20 mM HEPES pH 7.3+1.25 mM Probenecid (sodium salt) (NW-Assay Buffer). Dissolve 25 μg thallium ion indicator (also referred to herein as a "dye") in 25 μl DMSO containing 7% (w/v) Pluronic F-127. Add 12.5 μl of the dissolved thallium ion indicator to 10 ml Probenecid Assay Buffer (NW-Dye Loading Solution). Add 20 μl/well of Dye Loading Solution to the Cell Plate. Incubate the Cell Plate containing Dye Loading Solution for 1 hour at room temperature (Dye Loaded Cell Plate). Prepare a 384-well, polypropylene plate containing 40 μl/well of NW-Assay Buffer where 120 mM potassium chloride replaces 120 mM of the sodium chloride in the buffer (120 K NW-Assay Buffer) containing a range of concentrations of dofetilide, a known hERG inhibitor (Compound Plate). Transfer 20 μl/well of samples from the Compound Plate to the Dye Loaded Cell Plate (Compound Treated Cell Plate). Incubate the Compound Treated Cell Plate for 20 minute at room temperature. Prepare a Stimulus Plate using a 384-well, polypropylene plate containing 40 μl/well of a buffer containing 125 mM sodium gluconate, 2.4 mM thallium sulfate, 1 mM magnesium sulfate, 1.8 mM calcium gluconate, 5 mM glucose, 10 mM HEPES, pH 7.3. (Stimulus Buffer). Transfer both the Compound Treated Cell Plate and the Stimulus Plate to a Hamamatsu FDSS and execute a Data Acquisition Protocol where images of the Compound Treated Cell Plate are acquired every 1 second with an excitation wavelength of 470±20 nm, and an emission wavelength of 540±20 nm. Acquire images for 10 seconds. At the 10 second time point during image acquisition, transfer 10 μl/well from the Stimulus Plate to the Compound Treated Cell Plate using the FDSS's internal pippettor to initiate thallium flux. Acquire images every 1 second with an excitation wavelength of 470±20 nm, and an emission wavelength of 540±20 nm for an additional 110 seconds. Analyze data representing the amplitude of the fluorescent signal for each well at each of the 120 time points acquired during the Data Acquisition Protocol using Microsoft Excel by first dividing the fluorescence values from each individual well at each time point by the fluorescent value for that well at the first time point (Normalized Fluorescence Values). Calculate slopes of the Normalized Fluorescence Values between the 12 second and 22 second time points (Slope Values). Average Slope Values from each of four wells containing the same concentration of dofetilide to arrive at Mean Slope Values for each dofetilide concentration. Calculate standard errors of the mean (SEM) for the corresponding data points. Fit Mean Slope Values to a four-parameter logistic equation using GraphPad Prism. Plot the Mean Slope Values+/−SEM and fits as shown in FIG. 2.

All of the U.S. patents, U.S. patent application publications, U.S. patent applications, foreign patents, foreign patent applications and non-patent publications referred to in this specification are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:
1. A compound of formula (I-a),
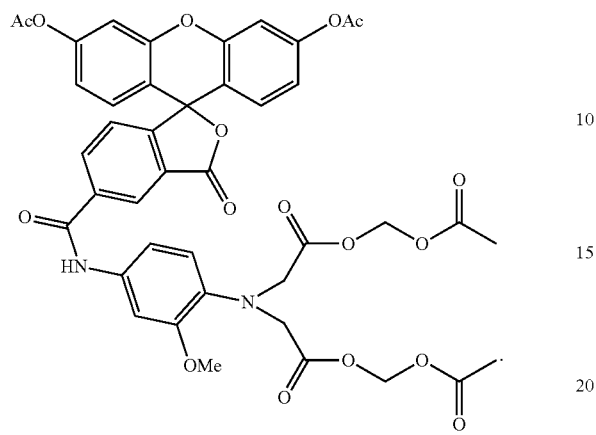
(I-a)